United States Patent [19]

Lee

[11] Patent Number: 5,192,791
[45] Date of Patent: Mar. 9, 1993

[54] FUSED RING HETEROCYCLES AND PHARMACEUTICAL COMPOSITIONS CONTAINING SAME

[75] Inventor: Sung J. Lee, Clarks Summit, Pa.

[73] Assignee: Biofor, Ltd., Waverly, Pa.

[21] Appl. No.: 551,457

[22] Filed: Aug. 14, 1990

Related U.S. Application Data

[62] Division of Ser. No. 248,942, Sep. 26, 1988, Pat. No. 4,958,482.

[51] Int. Cl.$^5$ .................... C07D 209/46; A61K 31/40
[52] U.S. Cl. .................................... 514/418; 548/406; 548/472; 548/482; 548/543; 546/140
[58] Field of Search ...................... 548/472, 482, 406; 546/140; 514/428

[56] References Cited

U.S. PATENT DOCUMENTS 4,166,125  8/1979  Kigasawa et al. ................. 548/472
4,954,514  9/1990  Kita et al. ........................... 548/252

*Primary Examiner*—David B. Springer
*Attorney, Agent, or Firm*—Joseph W. Molasky & Assocs.

[57] ABSTRACT

A novel class of pyrrolidin-2-one and piperidin-2-one compounds in which the nitrogen atom is bonded to an oxyphenyl radical having tertiary-alkyl and tri-methylsilyl substituents. The compounds possess anti-inflammatory, immunomodulatory, analgesic and anti-pyretic activity and they may be combined with excipients to provide formulations which are useful in treating arthritis and conditions associated with that disease.

20 Claims, No Drawings

FUSED RING HETEROCYCLES AND PHARMACEUTICAL COMPOSITIONS CONTAINING SAME

This is a division of application Ser. No. 248,942, filed Sep. 26, 1988, U.S. Pat. No. 4,958,482.

This invention relates to a novel class of pharmacologically active compounds which exhibit anti-inflammatory, immunomodulatory, analgesic and/or anti-pyretic activity.

This invention also relates to pharmaceutical compositions in which the instant products are combined with excipients to provide formulations useful in the treatment of inflammation, pain and/or fever.

Structurally, the compounds of this invention are pyrrolidines and piperidines which contain an oxo group at position 2 of the heterocyclic nucleus and, on the nitrogen atom, an oxyphenyl moiety substituted by tertiary-alkyl and trimethylsilyl radicals.

BACKGROUND OF THE INVENTION

Many attempts have been made to find a correlation between structure and activity in the treatment of anti-inflammatory diseases but no connection has been found and today researchers will agree only that arthritis is an incurable disease which defies any structure-activity relationships.

This was not always so. In 1980, I. L. Bonta[1] published a review entitled "Progress in Medicinal Chemistry" where he argued convincingly that an association exists between compounds having oxygen-containing radicals as, for example, the phenothiazines, steroids, sulphydryl compounds and copper complexes, and anti-inflammatory activity. This study led to the screening of many compounds as researchers sought to find some interdependence between known anti-oxidants and the effects which those agents produce.

This anti-oxidant theory ga ned credence in 1985 when K.F. Swingle[2] in an article entitled "Anti-Inflammatory Activity of Antioxidants" offered a rationale for using anti-oxidants to arrest and reverse the degenerative effects of arthritis in mammalian hosts. Swingle urged that since arachidonic acid, an unsaturated acid occurring naturally in fat, is known to undergo enzymatic oxidation in animals and produces pro-inflammatory prostaglandins, any compound which retards or prevents oxidation ought to be a candidate for treating arthritis and the dabilitating effects of that disease.

This theory remained in vogue until about 1986 when I. Katsumi reported in the "Chemical and Pharmaceutical Bulletin"[3] that an in-vivo study of several di-(tert-butyl)-phenols failed to support the anti-oxidant view. Support for this opinion also appears in a patent to G. Moore (U.S. Pat. No. 4,357,345) where it is stated in Column 1, lines 36-52, that the anti-oxidant activity of 3,5-di(tert-butyl)-4-hydroxytoluene, an additive used to extend the shelf-life of food, has little or no value as an anti-inflammatory agent. Moreover, the patentee notes that the absence of anti-inflammatory activity extends also to many other compounds which share the di-(tert-butyl)phenol structure as for example: 2,6-di-(tert-butyl)phenol, 4-carboxamido-2,6-di-(tert-butyl)phenol, 4-(2-chlorobenzoyl)-2,6-di-(tert-butyl)phenol, 4-(5-carboxy-2-chlorobenzoyl)-2,6-di-(tert-butyl)phenol, 2,6-di-(tert-butyl)-4-(phenylsulfonyl)phenol, 4-acetyl-2,6-(di-tert-butyl)phenol and 4-n-octyl-2,6-di-(tert-butyl)-phenol. As a result, G. Moore concluded that there is no correlation which can be drawn between compounds containing the di-(tert-butyl)phenol structure and inflammation and that the effectiveness of compounds in this field can only be ascertained by trial and error (Column 1, lines 63-66).

The lack of a correlation between anti-inflammatory activity and the di-tertiary butyl phenol structure is further supported by G. Bogdonov et al. Bogdonov reports in Khimiya Geterotsiklicheskikh Soedinenii, Vol. 12: pages 1660-1664 (1971) that certain [(3,5-di-tert-butyl-4-hydroxyphenyl)alkenyl]pyridines, specifically, 2-[2-(3',5'-di-tert-butyl-4'-hydroxyphenyl)ethenyl]pyridine and 4-[2-(3',5'-di-tert-butyl-4'-hydroxyphenyl)ethenyl]pyridine, are effective in the treatment of tumors: however, the authors fail to attribute to these compounds any evidence of anti-inflammatory effectiveness.

The literature, however, is not without reference to 2,6-di-tert-butylphenols bonded directly to a heterocyclic ring as shown, for example, in European Appln. No. 59,090. Moreover, Lazer in U.S. Pat. No. 4,743,606; Moore in U.S. Pat. Nos. 4,172,082 and 4,124,725 and Isomuda et al in Chem. Pharm. Bull. Vol 31: pages 3179-3185 (1983) describe a variety 2,6-di-tert-butyl-phenols bonded directly or indirectly to pyridine and other heterocyclic or aromatic nuclei; however, none of these are pyrrolidinones, piperidinones or functionally equivalent heterocycles bonded directly to a 2,6-di-tert-butylphenol moiety.

REFERENCES

1. I. L. Bonta et al; "Progress in Medicinal Chemistry", Vol. 17: page 228; Elsevier/North Holland, Amsterdam (1980).
2. K. F. Swingle et al; "Anti-Inflammatory and Anti-Rheumatic Drugs", Vol. III: Chapter 4 Entitled "Anti-Inflammatory Activity of Antioxidants": CRC Press, Inc., K. D. Rainsford, Editor (1935).
3. I. Katsumi et al; "Chemical and Pharmaceutical Bulletin", Vol. 34 [34]: pages 1619-1627 (1986).

SUMMARY OF THE INVENTION

The present invention is an advance in the art because it provides a new class of pharmacologically active compounds which are useful in treating arthritis and the degenerative conditions generally associated with that disease.

A further object provides for identifying compounds which have utility a immunomodulating agents, anti-inflammatory agents, analgesic agents and anti-pyretic agents.

A still further object provides for pharmaceutical compositions in which the aforementioned compounds are combined with excipients to afford formulations which are useful in treating diseases characterized by inflammation, pain and/or fever.

DETAILED DESCRIPTION

The products of this invention are compounds of the following general formula:

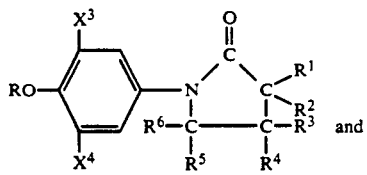

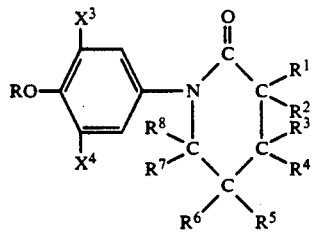

wherein:

R is a member selected from the group consisting of hydrogen, alkyl, alkanoyl and aroyl:

$R^1$, $R^2$, $R^3$, $R^4$, $R^5$, $R^6$, $R^7$ and $R^8$ (hereinafter, $R^1$-$R^8$) are the same or different and represent a member selected from the group consisting of hydrogen and lower alkyl with the proviso that when $R^1$ and $R^3$ represent hydrogen $R^2$ and $R^4$ may be joined to form a hydrocarbylene chain of four carbon atoms, that is, a divalent organic moiety comprised solely of carbon and hydrogen and containing four carbons between their points of attachment to the heterocyclic nucleus as, for example, 1,3-butadienylene (i.e., —CH=CH—CH=CH—) or tetramethylene;

$X^3$ and $X^4$ are the same or different and represent a member selected from the group consisting of tertiary-alkyl, for example, tert-lower alkyl such as tert-butyl, and trimethylsilyl; and Set forth below are definitions for $R^1$-$R^8$.

The term "alkyl" refers to a straight or branched chain alkyl of from about 1-10 carbon atoms. Typical of the alkyl radicals intended are, for example, methyl, ethyl, n-pentyl, isopentyl, hexyl, isohexyl, heptyl, octyl, nonyl and decyl.

The term "lower alkyl" refers to straight or branched chain alkyl of from about 1-5 carbon atoms such as methyl, ethyl, n-propyl, isopropyl, n-butyl, isobutyl, n-pentyl or isopentyl and the like.

The term "alkanoyl" refers to straight or branched chain aliphatic acyl moieties of from about 1-8 carbon atoms as, for example, formyl, acetyl, propionyl, isopropionyl, n-butyryl, isobutyryl, pentanoyl, n-heptanoyl or n-octanoyl and the like.

The term "aroyl" refers to mononuclear and binuclear aromatic acyl radicals as, for example, benzoyl or naphthoyl including aromatic nuclei in which the ring is substituted by one or more alkyl radicals as illustrated by 4-methyl-benzoyl and 2-methyl naphthoyl and the like.

Included within this invention are the non-toxic pharmacologically acceptable salts of the instant products as, for example, the metal salts. Suitable metal salts include, for example, the alkali metal or alkaline earth metal salts such as are derived from sodium hydroxide, sodium carbonate, potassium carbonate, potassium hydroxide or calcium carbonate and the like.

A preferred embodiment of this invention resides in those products wherein the heterocyclic nucleus is a pyrrolidin-2-one:

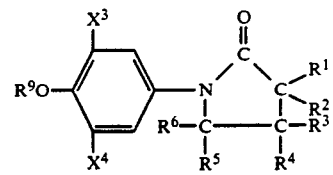

wherein:

$R^1$, $R^2$, $R^3$, $R^4$, $R^5$ and $R^6$ (hereinafter, $R^1$-$R^6$) are the same or different and represent a member selected from the group consisting of hydrogen and lower alkyl with the proviso that when $R^1$ and $R^3$ represent hydrogen $R^2$ and $R^4$ may be joined to form a hydrocarbylene chain of four carbon atoms, that is, a divalent organic moiety comprised solely of carbon and hydrogen and containing four carbons between their points of attachment to the heterocyclic nucleus as, for example, 1,3-butadienylene (i.e., —CH=CH—CH=CH) or tetramethylene:

$R^9$ is selected from the group consisting of hydrogen, lower alkyl, alkanoyl and aroyl;

$X^3$ and $X^4$ are the same or different and represent a member selected from the group consisting of tert-lower alkyl such as tert-butyl and trimethylsilyl; and the non-toxic pharmacologically acceptable salts thereof.

The foregoing compounds (I) are uniquely suited for treating the inflammatory effects of rheumatoid arthritis and osteoarthritis and constitute a preferred subgroup of compounds within this invention. Moreover, those compounds wherein $R^9$ is hydrogen exhibit an unexpectedly high order of activity and represent a particularly preferred subgroup of this invention.

Another preferred embodiment provides for products wherein the heterocyclic nucleus is a piperidin-2-one:

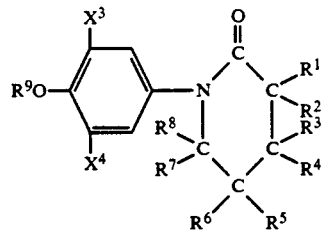

wherein:

$R^1$, $R^2$, $R^3$, $R^4$, $R^5$, $R^6$, $R^7$ and $R^8$ (hereinafter, $R^1$-$R^8$) are the same or different and represent a member selected from the group consisting of hydrogen and lower alkyl with the proviso that when $R^1$ and $R^3$ represent hydrogen $R^2$ and $R^4$ may be joined to form a hydrocarbylene chain of four carbon atoms, that is, a divalent organic moiety comprised solely of carbon and hydrogen and containing four carbons between their points of attachment to the heterocyclic nucleus as, for example, 1,3-butadienylene (i.e., —CH=CH—CH=CH—) or tetramethylene;

$R^9$ is selected from the group consisting of hydrogen, lower alkyl, alkanoyl and aroyl;

$X^3$ and $X^4$ are the same or different and represent a member selected from the group consisting of tertiary-alkyl, for example, tert-lower alkyl such as tert-butyl, and trimethylsilyl: and the non-toxic pharmacologically acceptable salts thereof.

The above-identified compounds (II) are also uniquely suited for treating the inflammatory effects of rheumatoid arthritis and osteoarthritis and their low toxicity makes them particularly effective in the treatment of those diseases. Moreover, those compounds wherein $R^9$ is hydrogen exhibit an unexpectedly high order of activity and this effect, combined with their low toxicity, makes them an especially preferred subgroup of compounds within this invention.

Still another embodiment relates to fused ring products of the following structure:

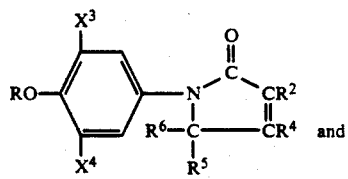   III

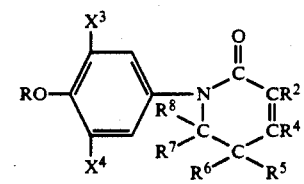   IIIa wherein:

R is a member selected from the group consisting of hydrogen, alkyl, alkanoyl and aroyl, $R^2$ and $R^4$ represent hydrocarbyl radicals which are joined to form an unsaturated hydrocarbylene chain having four carbon atoms between their points of attachment to the heterocyclic ring;

$R^5$–$R^8$ are the same or different and represent a member selected from the group consisting of hydrogen and lower alkyl; and $X^3$ and $X^4$ are the same or different and represent a member selected from the group consisting of tertiary-alkyl and trimethylsilyl; and the non-toxic pharmacologically acceptable salts thereof.

Compounds within this class (III and IIIa, supra) exhibit a surprising effectiveness against the inflammatory effects associated with rheumatoid arthritis and osteoarthritis.

SYNTHESIS

The products of this invention are obtained by condensing a suitably substituted aniline with a haloalkanoic acid halide followed by cyclization of the resulting amide. This process is conducted at less than ambient temperatures, preferably, within a range of from about 0°–10° C.:

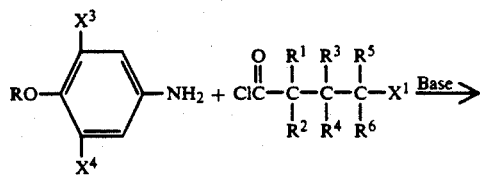   [Ia]

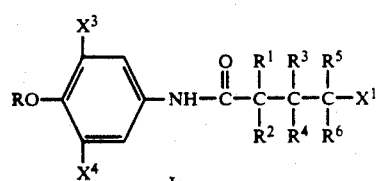   Ia

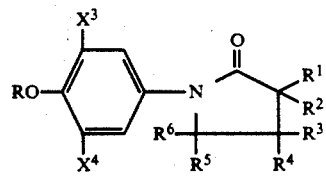

where R, $R^1$–$R^6$, $X^3$ and $X^4$ are as defined above and $X^1$ is halo such as chloro, bromo, fluoro or iodo and the like. The initial step in this process, that is, the condensation of the aniline and the 4-haloalkanoic acid halide, is catalyzed by the addition of a weak base such as pyridine and recovery is enhanced by conducting the reaction in a suitably inert solvent such as ether or tetrahydrofuran.

The second step in this process, that is, the conversion of the amide (Ia, supra) to the pyrrolidin-2-one, is also base-catalyzed following which a suitable acid as, for example, a mineral acid, is added to convert the resulting salt to the desired product (I). The preceding equation depicts the preparation of the pyrrolidin-2-one series of compounds (Ib) but this is for illustration only and the corresponding piperidin-2-ones are obtained in a similar manner by substituting the appropriate 5-haloalkanoic acid halide for the 4-haloalkanoic acid halide therein shown.

Those products wherein the pyrrolidinone or piperidinone ring is fused to an aromatic or cycloaliphatic nucleus as, for example, where R2 and R4 form a 1,3-butadienylene chain or a tetramethylene chain, may be obtained from their corresponding anhydrides. In this procedure, the anhydride precursor is condensed with a suitably substituted aniline with heating to afford an imide which, when treated with zinc and acetic acid under reflux, results in the formation of the desired product:

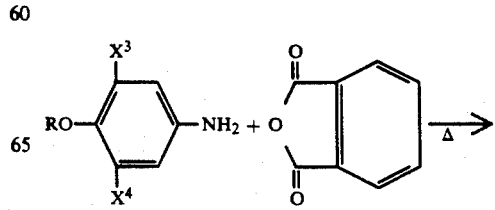

-continued

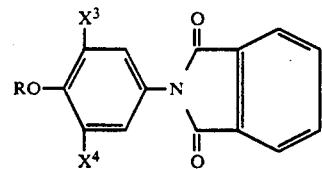

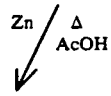

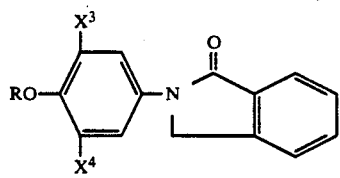

where R, $X^3$ and $X^4$ are as defined above and AcOH is acetic acid.

The products obtained by the foregoing methods may also be subjected to alkylation procedures so as to introduce onto the heterocyclic ring one or more alkyl moieties. One such method consists of treating the 1-(3,5-di-substituted-4-oxyphenyl)pyrrolidin-2-ones and 1-(3,5-di-substituted 4-oxyphenyl)piperidin-2-ones with an alkyl halide in the presence of lithium diisopropylamide and, thereafter, with a mineral acid. This method is particularly suitable for substituting a single alkyl for hydrogen on the heterocyclic nucleus but other known procedures may also be employed to provide a variety of mono-alkyl and poly-alkyl substituted derivatives.

An alternative method suitable for introducing alkyl in the 4-position of the pyrrolidinone ring consists of treating the aniline reactant with an alkenoic acid halide and then with a tri-alkyl sulphoxonium halide. In this process the aniline and alkenoic acid halide form an alkenamide and the tri-alkyl sulphoxonium halide with base in solution forms a di-alkyl sulphoxonium methylide. The following equation wherein the methylide is dimethylsulphoxonium iodide illustrates this process:

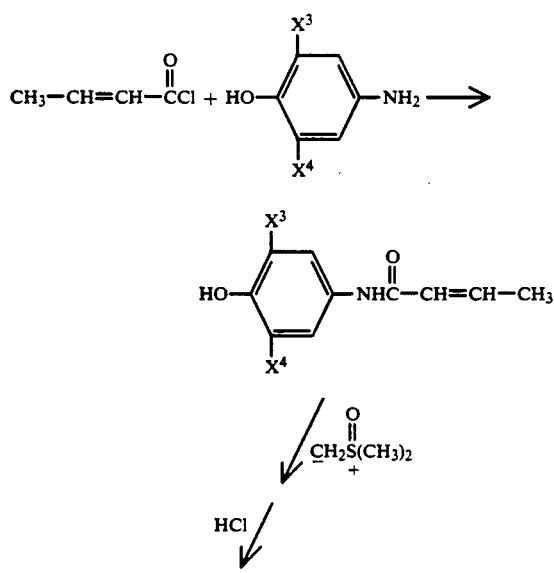

-continued

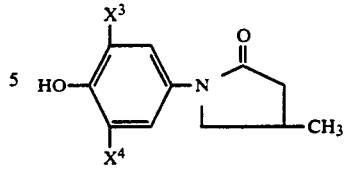

wherein $X^3$ and $X^4$ are as defined above.

PHARMACOLOGY

The compounds (I) of this invention and their non-toxic salts are effective in the treatment of inflammation, pain and/or fever in various test systems. Moreover, they exhibit a high level of activity over prolonged periods with little or no evidence of toxicity.

Compounds which have proven to be particularly useful in treating inflammation and inflammatory diseases such as rheumatoid arthritis and osteoarthritis are those of the following subgroup:

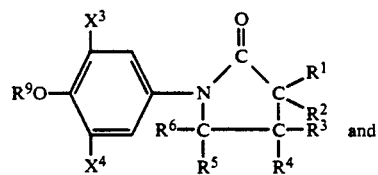

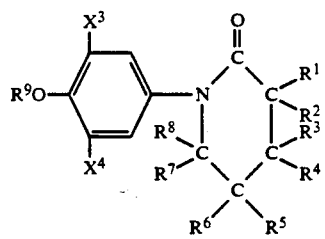

wherein:

$R^1-R^8$ are the same or different and represent a member selected from the group consisting of hydrogen and lower alkyl with the proviso that when $R^1$ and $R^3$ represent hydrogen $R^2$ and $R^4$ may be joined to form a hydrocarbylene chain having four carbon atoms between their points of attachment to the heterocyclic ring;

$R^9$ is selected from the group consisting of hydrogen, lower alkyl, alkanoyl and aroyl; and $X^3$ and $X^4$ are the same or different tertiary-lower alkyl moieties; and the non-toxic pharmacologically acceptable salts thereof.

The compounds identified as I and II, supra, exhibit surprisingly good anti-inflammatory activity and very favorable therapeutic indexes even at low dosage levels and they maintain their effectiveness over prolonged periods.

Assay: The pharmacological properties of the present compounds were determined by assay procedures which measured their ability to evoke a characteristic response in test animals.

Anti-Inflammatory: This activity was evaluated via a modification of the Adjuvant Arthritis Assay (AA) described by S. Wong et al in "The Journal of Pharmacology and Experimental Therapeutics", Vol. 185, No. 1: pages 127-128 (1973). This assay measures the ability of the test compound to antagonize local edema, a characteristic of the inflammatory response.

Analgesic: The "Acetylcholine Writhing Assay" (ACH) of Collier et al [Nature; Vol. 204: page 1316 (1964)] was employed. In this study the test compounds were administered orally to mice and 45 minutes later the mice were injected with acetylcholine. The frequency of writhing was counted in each animal and the response elicited in the drug-treated mice was compared with the response of those given acetylcholine alone.

Immunomodulatory: This activity was determined by using a Modified Adjuvant Assay procedure in which female rats were injected with *Mycobacterium butyricum* to induce hind paw edema. The test compounds were administered orally and the difference in volume between dosed and non-dosed paws was determined.

Antipyretic: This activity was evaluated by creating a yeast-induced fever in rats according to a modified method of the procedure described by Loux et al in "Toxicology and Applied Pharmacology", Vol. 22: page 672 (1972). In this assay rats injected with yeast in distilled water were dosed with test compounds, aspirin (positive control) and a vehicle (negative control) and the observed differences in body temperature were analyzed statistically.

Antiarthritic: Chronic anti-inflammatory and antiarthritic activities were determined according to the method described by S. Wong in "Tolmetin: A New Non-Steroidal Anti-inflammatory Agent", Editor: John R. Ward, Excerpta Medica, N.J., pages 1-27 (1976). In this assay the differences between dosed and non-dosed paw values were determined postadjuvant.

Formulation: The products (I) of this invention may be employed as the active ingredient in a variety of pharmaceutical compositions in admixture with a pharmaceutically acceptable solid or liquid diluent or carrier. Pharmaceutically acceptable diluents or carriers include any non-toxic substance which, when mixed with a product of this invention renders it more suitable for administration either orally, intravenously or intermuscularly. Typical of the diluents or carriers intended are solid, liquid and semi-solid diluents and carriers such as paraffins, vegetable oils, mannitol, sucrose, glucose or sterile liquids such as water, saline, glycols and oils of a petroleum, animal, vegetable or synthetic origin as, for example, peanut oil, mineral oil and sesame oil. Moreover, the composition may be enhanced by including other useful ingredients such as stabilizers, binders, antioxidants, preservatives, lubricators, suspending agents, viscosity aids or flavoring agents and the like.

The compositions may also include one or more other ingredients having pharmacological activities of their own so as to provide a broad spectrum of activity. For example, in the treatment of inflammation one common complication is the occurrence of edema a condition which may be alleviated by combining a compound of this invention with an appropriate diuretic and/or anoretic. The nature and quantity of these added ingredients will depend largely upon the malady to be treated and the weight of the patient and, therefore, the precise nature of the composition must be left to the practitioner to determine.

Dosage: The dose to be administered depends on a large extent upon the condition being treated and the weight of the host; however, a general daily dosage may consist of from about 0.1 mg to 500 mg. of active ingredient per kilogram of body weight which may be administered in a single dose or multiple doses. A total preferred daily dose lies in the range of from about 0.25 mg to 100 mg of active ingredient per kilogram of body weight.

Unit Dosage Forms: The compositions of this invention may be administered parenterally or orally in solid and liquid oral unit dosage form as, for example, in the form of tablets, capsules, powders, suspensions, solutions, syrups, sustained release preparations and fluid injectable forms such as sterile solutions and suspensions. The term "unit dosage form" as used in this specification refers to physically discrete units which are administered in single or multiple dosages, each unit containing a predetermined quantity of active ingredient in combination with the required diluent, carrier or vehicle.

Solid Tablets: Hard tablets are prepared by combining the active ingredient, suitably comminuted, with a diluent such as starch, sucrose, kaolin or calcium phosphate and a lubricant. Optionally, the compositions may contain stabilizers, anti-oxidants, preservatives, suspending agents, viscosity aids, flavoring agents and the like. The composition is pressed into tablets and a protective coating of shellac, wax, sugar or polymeric material is added. If desired, dyes can also be included to provide a color-code means for distinguishing between different dosages.

Chewable Tablets: This unit dosage form is prepared by combining the active ingredient with a pharmaceutically acceptable orally ingestible solid carrier and a gum base. If desired, the composition may also contain flavors, binders, lubricants and other excipients.

Soft Capsule: Soft gelatin capsules are prepared by dissolving the active ingredient in a pharmaceutically acceptable oil such as peanut oil, sesame oil or corn oil together with glycerine and water.

Hard Capsule: Hard gelatin capsules may be prepared by mixing the active ingredient with lactose and magnesium stearate and placing the mixture in a No. 3 gelatin capsule. If desired, a glidant such as colloidal silica may also be added to improve flow properties and a distintegrating or solubilizing agent may be included to improve the availability of the medicament upon injection.

Liquids: Syrups, elixirs and suspensions can be prepared in unit dosage form so that the compositions can be administered by the teaspoonful. Syrups are prepared by dissolving the compounds in a suitably flavored aqueous sucrose solution, whereas, elixirs are prepared by containing the active ingredient with non-toxic alcoholic vehicles. Suspensions are obtained by mixing a dry powder containing the active ingredient in water with a minor amount of a suspending agent, a flavoring agent, a sweetener such as sugar and a preservative if necessary.

Parenteral: Unit dosage forms suitable for parenteral administration are prepared by suspending or dissolving a measured amount of the active ingredient in a non-toxic liquid vehicle suitable for injection such as an aqueous or oleaginous medium and sterilizing the resulting mixture.

Alternatively, a measured amount of the active ingredient may be placed in a vial as a discrete entity and the vial and its contents can be sterilized and sealed. If desired, an accompanying vial containing an appropriate vehicle for admixture with said active ingredient can also be provided so that the contents of both vials can be combined and mixed for administration purposes immediately prior to use.

Topical: Powders and other solid unit dosage forms can be formulated by combining an active ingredient of this invention with a suitable carrier such as talc, bentonite, silicic acid, polyamide powder, animal and vegetable fats, wax, paraffins, starch, tragacanth, cellulose derivatives, polyethylene glycols, silicones and zinc oxide or mixtures thereof.

Liquid and semi-liquid formulations, on the other hand can be prepared in the form of suspensions, solutions, ointments, pastes, creams and gels by combining an active ingredient with such carriers as polyethylene glycol, vegetable and mineral oils, alcohols such as isopropanols and the like.

In addition to the aforementioned carriers the formulations can also include such other excipients as emulsifiers, preservatives, colorants, perfumes and the like.

The pH of the formulation should approximate values suitable for application to normal skin, that is, the formulation should possess a pH range of from about 6-6.5 and buffers may be added to the composition to achieve and maintain this pH range. Typical of a buffer which may be used for this purpose is, for example, an aqueous mixture of acetic acid and sodium lactate. The water employed in preparing this buffer should be distilled or demineralised to ensure dermatological acceptability.

EXAMPLE 1

1-(3,5-Di-tert-Butyl-4-Hydroxyphenyl)Pyrrolidin-2-One

Step A:
N-(3,5-Di-tert-Butyl-4-Hydroxyphenyl)-4-Chlorobutyramide

To a stirred mixture of 65.2 g (295 mmol) of 3,5-di-tert-butyl-4-hydroxyaniline and 23.3 g (295 mmol) of pyridine in 700 ml of ether cooled to 3° C. there was slowly added 41.6 g (295 mmol) of 4-chlorobutyryl chloride. Fifteen hours later 700 ml of ethyl acetate was added and the mixture was washed successively with 500 ml of water, 500 ml of dilute sodium bicarbonate solution and again with 500 ml of water. The organic phase was dried over anhydrous magnesium sulfate and concentrated to a solid (85.3 g). This solid was triturated in hexane and filtered to yield 75.2 g of N-(3,5-di-tert-butyl-4-hydroxyphenyl)-4-chlorobutyramide.

$^1$HNMR(CDCl$_3$): δ 1.43(s,18H), 2.20(quintet,2H), 2.53 (t,2H), 3.67(t,2H), 5.08(s,1H), 7.15(broad s,1H), 7.32(s,2H).

Step B:
1-(3,5-Di-tert-Butyl-4-Hydroxyphenyl)Pyrrolidin-2-One

The N-(3,5-di-tert-butyl-4-hydroxyphenyl)-4-chlorobutyramide (75 g; 230 mmol) in 100 ml of tetrahydrofuran was added slowly to a stirred suspension of 20 g (500 mmol) of 60% sodium hydride in mineral oil (washed twice with 200 ml portions of hexane) in 1000 ml of ether cooled to 4° C. The reaction mixture became deep blue in color and gas evolution was observed. Fifteen hours later an additional 2 g of 60% sodium hydride in mineral oil dispersion (washed with hexane) was added to the reaction mixture together with 250 ml of tetrahydrofuran. After nine hours the reaction mixture was cooled to 10° C. and 250 ml of 1N hydrochloric acid was added slowly. The mixture was concentrated to 300 ml in vacuo and diluted with 700 ml of ethyl acetate and 700 ml of water. The organic phase was separated, dried over anhydrous magnesium sulfate and concentrated to yield 75.2 g of solid. This solid was recrystallized from acetone to yield 32.4 g solid product having a melting point of 170°-173° C. The mother liquor was chromatographed on silica gel with 40% ethyl acetate-hexane to afford an additional 18.8 g of solid product having a melting point of 171°-174° C. The two batches of product were combined and recrystallized from acetone to yield 39.8 g (137 mmol) of pure 1-(3,5-di-tert-butyl-4-hydroxyphenyl)pyrrolidin-2-one, mp 173°-175° C.

$^1$HNMR(CDCl$_3$): δ 1.43(s,18H), 2.1(quintet,2H), 2.58 (t,2H), 3.83(t,2H), 5.14(s,1H), 7,31(s,2H);

$^{13}$CNMR(CDCl$_3$): δ 18.39, 30.40, 32.63, 34.76, 50.09, 119.19, 131.87, 136.83, 151.77, 174.57; IR (KBr) cm$^{-1}$3395(ms), 2935(ms), 1665(s), 1594(w), 1427(ms), 1351(w), 1312(w), 1276(mw), 1225(ms), 1103(ms).

Analysis: C$_{18}$H$_{27}$NO$_2$:
Calculated: C,74.70; H,9.40; N,4.84.
Found : C,75.03: H,9.61: N,4.85.

EXAMPLE 2

1(3,5-Di-tert-Butyl-4-Hydroxyphenyl)Piperidin-2-One

Step A:
N-(3,5-Di-tert-Butyl-4-Hydroxyphenyl)-5-Chlorovaleramide

To a stirred mixture of 3.6 g (16 mmol) of 3,5 -di-tert-butyl-4-hydroxyaniline and 1.3 g (16 mmol) of pyridine in 50 ml of ether cooled to 0° C. there was slowly added 2.5 g (16 mmol) of 5-chlorovalerylchloride. The reaction mixture was allowed to warm to 25° C. and stirred for 15 hours following which the mixture was diluted with 100 ml of ether, washed with water, dried over anhydrous magnesium sulfate and concentrated to 5.8 g of solid. The solid was triturated in hexane and filtered to yield 5.5 g (16 mmol) of N-(3,5-di-tert-butyl-4-hydroxyphenyl)-5-chlorovaleramide.

Step B:
1-(3,5-Di-tert-Butyl-4-Hydroxyphenyl)-Piperidin-2-One

N-(3,5-di-tert-butyl-4-hydroxyphenyl)-5-chlorovaleramide (5.5 g: 16 mmol) in 25 ml of tetrahydrofuran was slowly added to 1.4 g (35 mmol) of 60% sodium hydride in mineral oil (washed twice with 25 ml portions of hexane) and 50 ml of tetrahydrofuran. The reaction mixture was stirred and gas evolution was observed. Seventeen hours later the mixture was concentrated to 20 ml, diluted with 50 ml of methylene chloride and washed successively with dilute 1N hydrochloric acid and dilute sodium bicarbonate solution. The organic phase was dried over anhydrous magnesium sulfate and concentrated to a solid (4.5 g). This solid was recrystallized from acetone to yield 3.9 g (12.8 mmol, 80%) of crystalline 1-(3,5-di-tert-butyl-4-hydroxyphenyl)piperidin-2-one, mp 212°-214° C.

$^1$HNMR(CDCl$_3$): δ 1.45(s,18H), 1.93(m,4H), 2.54(m,2H), 3.58(m,2H), 5.19(s,1H), 6.99(s,2H).

EXAMPLE 3

N-(3,5-Di-tert-Butyl-4-Hydroxyphenyl)Isoindolinone

Step A:
N-(3,5-Di-tert-Butyl-4-Hydroxyphenyl)Phthalimide

A mixture of 8.8 g (40 mmol) of 3,5-di-tert-butyl-4-hydroxyaniline and 5.9 g (40 mmol) of phthalic anhydride in 100 ml of tetrahydrofuran was refluxed for 24 hours. Concentrated hydrochloric acid (0.5 ml) was added and the mixture was refluxed for an additional seventeen hours and concentrated in vacuo. The resulting solid (13.2 g) was washed successively with water and hexane and then recrystallized from acetone-hexane to yield 10.9 g (31 mmol, 77%) of N-(3,5-di-tert-butyl-4-hydroxyphenyl)phthalimide, mp 196°–201° C.

$^1$HNMR(CDCl$_3$): δ 1.45(s,18H), 5.36(s,1H), 7.14(s,2H), 7.86(m,4H).

Step B:
N-(3,5-Di-tert-Butyl-4-Hydroxyphenyl)Isoindolinone

A mixture of 9.5 g (27 mmol) of N-(3,5-di-tert-butyl-4-hydroxyphenyl)phthalimide and 9 g of zinc dust in 100 ml of glacial acetic acid was refluxed for 20 hours. The reaction mixture was filtered and the filtrate concentrated in vacuo to a solid which was washed with dilute sodium bicarbonate solution, followed by washing with water to yield 7.9 g of a solid. This solid was recrystallized from acetone-hexane to yield 4.5 g (13.3 mmol, 49%) of pure N-(3,5-di-tert-butyl-4-hydroxyphenyl)isoindolinone, mp 205°–207° C.

$^1$HNMR(CDCl$_3$): δ 1.48(s,18H), 4.84(s,2H), 5.19(s,1H), 7.47–7.90(m,6H).

EXAMPLE 4

1(3,5-Di-tert-Butyl-4-Hydroxyphenyl)-3-Methyl-Pyrrolidin-2-One

To a solution of 1-(3,5-di-tert-butyl-4-hydroxyphenyl)pyrrolidin-2-one (2.5 g; 8.7 mmol) in 50 ml of tetrahydrofuran cooled to −60° C. there was slowly added 11.5 ml of 1.5M lithium diisopropylamide mono-tetrahydrofuran/cyclohexane solution. Ten minutes later, 12.5 g (8.8 mmol) of methyl iodide was added and the cooling bath was removed. Twenty five minutes later at −10° C., the reaction mixture was quenched with 20 ml of 1N hydrochloric acid and concentrated to approximately 25 ml in vacuo. Methylene chloride (50 ml) and 30 ml of water were added. The organic phase was separated, dried over anhydrous magnesium sulfate and concentrated to yield 3.1 g of solid. This solid was chromatographed on silica gel with 40% ethyl acetate-hexane and after trituration with hexane there was obtained 1.5 g (4.9 mmol, 57%) of a product identified as 1-(3,5-di-tert-butyl-4-hydroxyphenyl)-3-methyl-pyrrolidin-2-one, mp 164°–166° C.

$^1$HNMR(CDCl$_3$): δ 1.30(d,3H), 1.44(s,18H), 1.76(m,1H), 2.36(m,1H), 2.63(m,1H), 3.76(m,2H), 5.11(s,1H), 7.39(s,2H).

$^{13}$CNMR(CDCl$_3$): δ 16.44, 27.44, 30.42, 34.78, 38.33, 47.54, 118.38, 121.24, 132.27, 136.75, 151.43.

EXAMPLE 5

1-(3,5-Di-tert-Butyl-4-Hydroxyphenyl)-4-Methylpyrrolidin-2-One

Step A:
N-(3,5-Di-tert-Butyl-4-Hydroxyphenyl)-2-Butenamide

Crotonyl chloride (4.7 g, 45 mmol) in 10 ml of methylene chloride was added slowly to a stirred solution of 10 g (45 mmol) of 3,5-di-tert-butyl-4-hydroxyaniline in 50 ml of methylene chloride at 0° C. Ten minutes later 3.6 g (45 mmol) of pyridine was added and, after three hours, the mixture was filtered. The filtered solid was washed with water and triturated in ether to yield 5.4 g of N-(3,5-di-tert-butyl-4-hydroxyphenyl)-2-butenamide having a melting point of 215°–218° C.

$^1$HNMR(CDCl$_3$): δ 1.42(s,18H), 1.89(m,3H), 5.07(s,1H), 5.94(m,1H), 6.95(m,1H), 7.12(s,1H), 7.38(s,2H).

Step B:
1-(3,5-Di-tert-Butyl-4-Hydroxyphenyl)-4-Methylpyrrolidin-2-One

Trimethyl sulphoxonium iodide (5.9 g, 27 mmol) was added to 5.2 g (45 mmol) of 35% potassium hydride in an oil dispersion (previously washed with pentane) in 25 ml of tetrahydrofuran at 0° C. Ten minutes later, 5.2 g (18 mmol) of N-(3,5-di-tert-butyl-4-hydroxyphenyl)-2-butenamide dissolved in 100 ml of tetrahydrofuran was added and the mixture was allowed to warm to room temperature. Twenty four hours later, 10 ml of ethanol was added and the mixture was made acidic by the addition of 1N hydrochloric acid. The acidic mixture was concentrated to 50 ml, diluted with 100 ml of ethyl acetate and 50 ml of water and the organic phase was separated, dried over anhydrous magnesium sulfate and concentrated to a solid. The solid was chromatographed on silica gel with methylene chloride and triturated in pentane to afford 0.76 g of 1-(3,5-di-tert-butyl-4-hydroxyphenyl)-4-methylpyrrolidin-2-one, mp 157°–159° C.

$^1$HNMR(CDCl$_3$): δ 1.20(d,3H), 1.44(s,18H), 2.15–2.30 and 2.65–2.80(m,2H), 2.55(m,1H), 3.37–3.46 and 3.85–3.94(m,2H), 5.12(s,1H), 7.32(s,2H).

$^{13}$CNMR(CDCl$_3$): δ 19.75, 26.70, 30.40, 34.65, 34.75, 41.00, 118.87, 131.97, 136.84, 151.63, 174.06. IR(KBr)cm$^{-1}$ 3400(m broad), 2945(ms), 1661(s), 1593(w), 1429(ms), 1348(mw), 1224(ms), 1129(ms).

The pyrrolidin-2-one products of this invention may be obtained by following the procedure described in Example 1, Steps A and B and, together with Table I, infra, illustrates the aniline and alkanoyl halide starting materials employed in this process and the products obtained thereby:

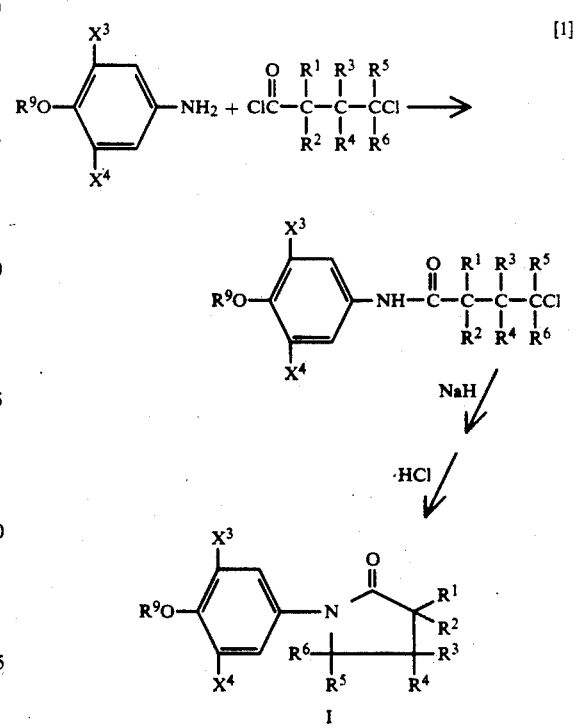

TABLE I

| Ex. | R⁹ | R¹ | R² | R⁴ | R³ | R⁵ | R⁶ | X³ | X⁴ |
|---|---|---|---|---|---|---|---|---|---|
| 6 | —COCH₃ | H | —CH=CH—CH=CH— | | H | H | H | —C(CH₃)₃ | —C(CH₃)₃ |
| 7 | 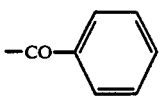 | H | H | H | H | H | H | —C(CH₃)₃ | —C(CH₃)₃ |
| 8 | —COCH₃ | H | H | H | H | H | H | —C(CH₃)₃ | —C(CH₃)₃ |
| 9 | H | H | H | H | —CH₃ | —CH₃ | H | —C(CH₃)₃ | —C(CH₃)₃ |
| 10 | H | —CH₃ | —CH₃ | H | H | H | H | —C(CH₃)₃ | —C(CH₃)₃ |
| 11 | H | H | H | H | H | H | —CH₃ | —C(CH₃)₃ | —C(CH₃)₃ |

When, in the preceding equation, R⁹ is hydrogen (Examples 9-11), the resulting 1-(3,5-di-substituted-4-hydroxyphenyl)pyrrolidin-2-one products may be converted to their corresponding 4-alkoxyphenyl, 4-alkanoyloxyphenyl and 4-aroyloxyphenyl derivatives by etherification procedures which are known in the art as, for example, by treatment with an alkali metal hydride such as sodium hydride and an alkyl halide, alkanoyl halide and aroyl halide according to the "Williamson" synthesis. The following equation and Table II illustrate this etherification procedure and the products obtained thereby:

When R¹⁰ is methyl, an enhanced yield of product may be obtained by substituting methyl iodide for methyl chloride in an otherwise similar procedure.

TABLE II

| Ex. | R¹ | R² | R³ | R⁴ | R⁵ | R⁶ | R¹⁰ | X³ | X⁴ |
|---|---|---|---|---|---|---|---|---|---|
| 12 | H | H | —CH₃ | H | —CH₃ | H | —CH₃ | —C(CH₃)₃ | —C(CH₃)₃ |
| 13 | —CH₃ | —CH₃ | H | H | H | H | n-C₃H₇ | —C(CH₃)₃ | —C(CH₃)₃ |
| 14 | H | H | H | H | H | —CH₃ | —C₂H₅ | —C(CH₃)₃ | —C(CH₃)₃ |
| 15 | —CH₃ | —CH₃ | H | H | H | H | —COCH₃ | —C(CH₃)₃ | —C(CH₃)₃ |
| 16 | H | H | H | H | H | —CH₃ | 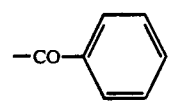 | —C(CH₃)₃ | —C(CH₃)₃ |

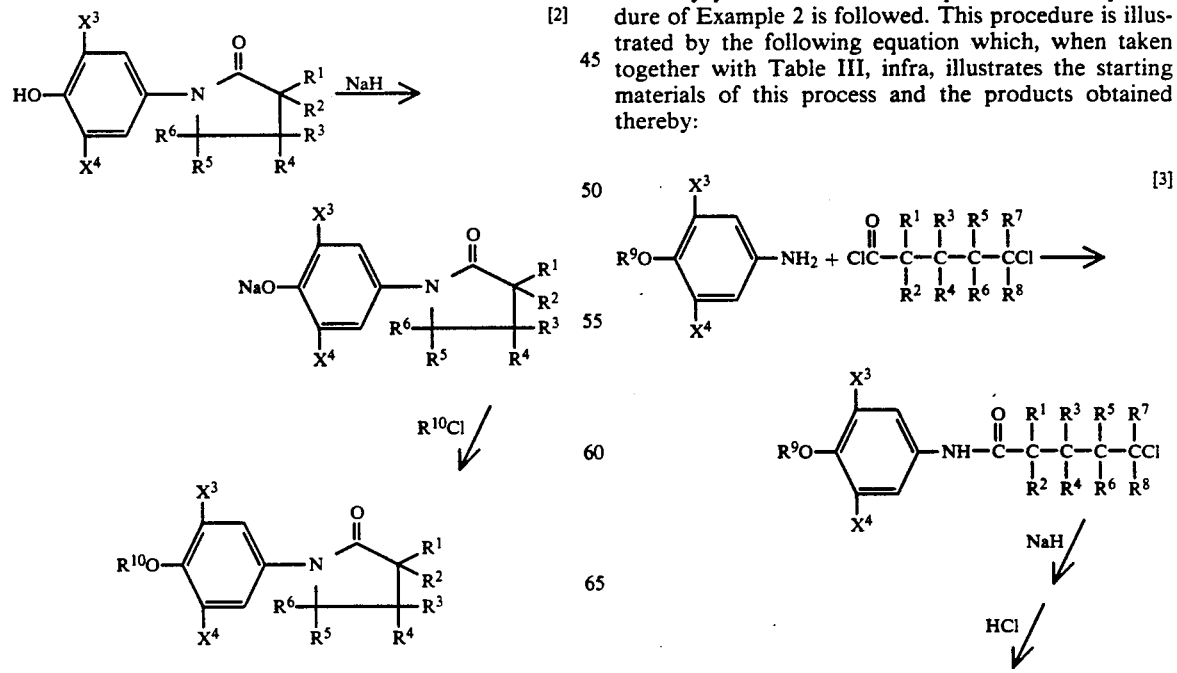

In piperidin-2-ones of this invention are obtained in a manner similar to that described in equation [1] except that a 5-halovaleryl chloride is substituted for the 4-halobutyryl chloride therein depicted and the procedure of Example 2 is followed. This procedure is illustrated by the following equation which, when taken together with Table III, infra, illustrates the starting materials of this process and the products obtained thereby:

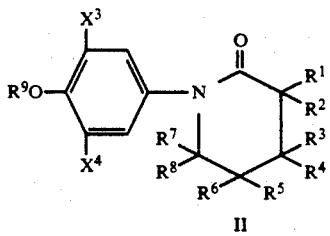

II

TABLE III

| Ex. | $R^9$ | $R^1$ | $R^2$ | $R^3$ | $R^4$ | $R^5$ | $R^6$ | $R^7$ | $R^8$ | $X^3$ | $X^4$ |
|---|---|---|---|---|---|---|---|---|---|---|---|
| 17 | H | —C$_2$H$_5$ | H | H | H | H | H | H | H | —C(CH$_3$)$_3$ | —C(CH$_3$)$_3$ |
| 18 | —COCH$_3$ | H | H | H | H | H | H | H | H | —C(CH$_3$)$_3$ | —C(CH$_3$)$_3$ |
| 19 | —CO-C$_6$H$_5$ | H | H | H | H | H | H | H | H | —C(CH$_3$)$_3$ | —C(CH$_3$)$_3$ |
| 20 | H | H | H | —CH$_3$ | H | H | H | H | H | —C(CH$_3$)$_3$ | —C(CH$_3$)$_3$ |
| 21 | H | H | H | H | H | H | H | —CH$_3$ | H | —C(CH$_3$)$_3$ | —C(CH$_3$)$_3$ |

In Table III those products where R is hydrogen, that is, the 1-(3,5-di-substituted-4-hydroxyphenyl)piperidin-2-ones of Examples 17, 20 and 21, may also be converted to their corresponding 4-alkoxyphenyl, 4-alkanoyloxyphenyl and 4-aroyloxyphenyl derivatives via treatment with sodium hydride and the appropriate alkyl halide, alkanoyl halide and aroyl halide as shown in equation [2], supra.

EXAMPLE 22

1-(3,5-Di-tert-Butyl-4-Methoxyphenyl)Pyrrolidin-2-One

To a stirred mixture of 0.3 g (7.5 mmol) of 60% sodium hydride in a mineral dispersion previously washed with hexane, in 20 ml of dimethylsulfoxide, there was added 2 g (6.9 mmol) of 1-(3,5-di-tert-butyl-4-hydroxyphenyl)-pyrrolidin-2-one. Gas evolution was observed. Twenty minutes later, 1 g (7 mmol) of iodomethane was added. The reaction mixture was stirred for thirty minutes and then diluted with 70 ml of water. The precipitated solid was collected by filtration and recrystallized from acetone-hexane to yield 1.7 g (5.6 mmol) of 1-(3,5-di-tert-butyl-4-methoxyphenyl)pyrrolidin-2-one, melting point 90°–91° C.

$^1$HNMR(CDC$_3$): δ 1.43(s,18H), 2.14(pentet,2H), 2.58 (t,2H), 3.67(s,3H), 3.85(t,2H), 7.44(s,2H)

$^{13}$CNMR(CDCl$_3$): δ 18.33, 32,24, 32.84, 36.24, 49.52, 64.55, 119.64, 134.64, 144.46, 157.05 and 174.54. IR(KBr)cm$^{-1}$ 3245(ms), 1684(ms), 1586(m), 1449(m3), 1413(ms), 1379(m), 1314(m), 1265(m), 1211(ms), 1167(mw), 1125(mw), 1009(m).

The following embodiments illustrate the preparation of typical unit dosage forms, it being understood that other active ingredients, other excipients and other vehicles may be substituted therefor to provide a variety of formulations suitable for oral and/or parenteral administration.

EXAMPLE 23

Dry Filled Capsule

A dry filled capsule is prepared by mixing the following ingredients:

| Ingredient | Mg. Per Capsule |
|---|---|
| 1-(3,5-Di-tert-butyl-4-hydroxyphenyl)pyrrolidin-2-one | 500 |
| Lactose | 225 |
| Magnesium Stearate | 10 |

The 1-(3,5-di-tert-butyl-4-hydroxyphenyl)pyrrolidin-2-one is reduced to a No. 60 powder. Lactose and magnesium stearate are passed through a No. 60 bolting cloth onto the powder and the combined ingredients are admixed for ten minutes and filled into a suitable gelatin capsule.

EXAMPLE 24

Compressed Tablet

A compressed tablet suitable for swallowing is prepared by mixing the following ingredients:

| Ingredients | Mg. Per Tablet |
|---|---|
| 1-(3,5-Di-tert-butyl-4-hydroxyphenyl)piperidin-2-one | 200 |
| Lactose (U.S.P. No. 80 powder) | 100 |
| Cornstarch | 50 |
| Magnesium Stearate | 5 |

The 1-(3,5-di-tert-butyl-4-hydroxyphenyl)piperidin-2-one and lactose are mixed thoroughly and granulated with starch paste. The granulated composition is passed through a No. 14 screen while still moist and dried at 45° C. in an oven. When drying is complete the dried material is passed several times through a No. 14 screen and cornstarch is added by passage through a No. 90 bolting cloth. This combination of ingredients is blended and magnesium stearate is added by passage through a No. 60 bolting cloth. The resulting mixture then is blended to a homogeneous mass and pressed into tablets weighing 355 mg per unit.

EXAMPLE 25

Oral Liquid

A liquid formulation suitable for oral administration is prepared from the following ingredients:

| Ingredients | |
|---|---|
| 1-(3,5-di-tert-butyl-4-hydroxyphenyl)pyrrolidin-2-one | 150 g |
| Sucrose | 200 g |
| Glucose | 100 g |
| Citric Acid | 13 g |
| Sodium Benzoate | 1.0 g |
| Concentrated Orange Oil | 0.2 ml |
| Purified Water, U.S.P. (Sufficent to | |

-continued

| Ingredients |
|---|
| produce 1000 mo) |

Sucrose and glucose are dissolved in 400 ml of water with heating following which the solution is cooled and citric acid, sodium benzoate and concentrated orange oil are added. The solution is brought to a volume of about 900 ml by the addition of water and 1-(3,5-di-tert-butyl-4-hydroxyphenyl)pyrrolidin-2-one is added. The solution is then filtered and brought to a volume of 1000 ml to provide a liquid suitable for oral administration.

EXAMPLE 26

Adjuvant Arthritis Assay: Developing

This anti-inflammatory study is a modification of the method described by Wong, et al in the Journal of Pharmacology and Experimental Therapeutics, Vol. 185, No. 1: pages 127-138 (1973).

The left and right rear paws of female Lewis rats (Charles River Laboratories) weighing 160-180 grams each were measured by mercury displacement prior to injection (Day Zero).

Adjuvant arthritis was induced in this rat colony by subcutaneous injection of *Mycobacterium butyricum* (0.75 mg in 0.1 ml light mineral oil, Fisher) using an automated Cornwall syringe. On days 11-15 post-adjuvant the injected animals with 0.25 to 0.75 ml. paw edema were selected and distributed evenly, according to edema size, into control and experimental groups of ten rats each. Vehicle control and drug treatments were assigned to the groups at random. The assay was performed using a variable dose level for each test compound per kilogram per day in 0.25% methylcellulose vehicle. All animals were dosed once daily for 4 days and on the fifth day both hind paw volumes were again measured using mercury displacement.

The hind paw edema was determined for each rat by subtracting the hind paw volume measured on Day Zero from the hind paw volume measured on the fifth day of the study. Group means were determined and the drug effect was calculated as percent inhibition of the hind paw edema according to the following equation:

$$\% \text{ Inhibition} = \frac{(\text{Mean Control Edema} - \text{Mean Experimental Edema})}{\text{Control Edema}} \times 100$$

The results of this study are set forth in Table IV below. The test compounds are identified by reference to the corresponding preparative examples, namely, 1-(3,5-di-tert-butyl-4-hydroxyphenyl)pyrrolidin-2-one (Example 1) and 1-(3,5-di-tert-butyl-4-hydroxyphenyl)-piperidin-2-one (Example 2). The known anti-inflammatory NAPROXEN was also tested for comparison purposes.

TABLE IV

| Adjuvant Arthritis | |
|---|---|
| Compound | ED$_{50}$ (mg/kg) |
| Example 1 | 21 |
| Example 2 | 34 |
| NAPROXEN | 28 |

Ulcerogenicity: No gastric or internal lesions were seen when the compound of Example 1 was administered orally to female Lewis rats once daily for four days at doses of up to 1000 mg/kg/day. The LD$_{50}$ for this compound is greater than 1000 mg/kg.

EXAMPLE 27

Adjuvant Arthritis Assay; Immunomodulatory

Lewis female rats were injected in the tail subcutaneously with *Mycobacterium butyricum* (0.75 mg in 0.1 ml light mineral oil, Fisher) on Day Zero. Prior to injection the volumes of the left and right rear paws were measured by mercury displacement. All rats were dosed orally with vehicle or test compounds on Day 5 to 9 inclusive. The volume of both hind paws were determined on Day 15 and the percent inhibitions were calculated based upon average edema on Day 15 relative to the edema mean in the control group.

TABLE V

| Adjuvant Arthritis Data-Immunomodulatory | | |
|---|---|---|
| Compound | Dosage | % Inhibition |
| Example 1 | 50 mg/kg | 39 |

EXAMPLE 28

Acetylcholine Writhing Assay

Analgesic activity was evaluated via the mouse acetylcholine writhing test using a modification of the procedure described by Collier, et al in Nature (New Biol.) Vol. 204; page 1316 (1964) and Br. J. Pharmacol, Chemother, Vol. 32: page 295 (1968). Each test group consisted of ten male CD-1 mice (Charles River Laboratories) weighing 18-28 grams each. Test compounds suspended in a mixture of 0.25% methylcellulose solution in olive oil were administered orally by gavage and forty five minutes later the mice were injected intraperitoneally with acetylcholine (0.55 mg/ml in 0.25% methylcellulose). The number of writhes in each group of mice were counted for 10 minutes immediately following the injection of acetylcholine and the percent inhibition was calculated as follows:

$$\text{Inhibition (\%)} = \left(1 - \frac{\text{Total number of writhes in test group}}{\text{Total number of writhes in control group}}\right) \times 100$$

Four dose levels were used to calculate the ED$_{50}$ of the test compound.

TABLE VI

| Acetylcholine Writhing Assay | |
|---|---|
| Compounds | ED$_{50}$ (mg/kg) |
| Example 1 | 13 |
| NAPROXEN | 6.2 |

EXAMPLE 29

Antipyretic Evaluation

Antipyretic activity was evaluated using a modification of the test described by Loux et al, in Toxicology and Applied Pharmacology, 22:672 (1972), that is, yeast-induced fever in rats. Each test group consisted of ten male Sprague-Dawley rats (Charles River Laboratories), weighing 180-225 grams each. Eighteen hours prior to compound administration the rats were weighed and body temperatures were recorded. Food was removed with water available ad libitum.

Each animal was injected subcutaneously into the central dorsal region with five (5.0) ml portions of a 15% (150 mg/1.0 ml) suspension of Fleischman's yeast in distilled water. Eighteen (18) hours after the yeast injection body weights and temperatures were taken and recorded and animals which exhibited an increase in body temperature greater than 1° C. were selected for the study.

Test compounds suspended in 0.25% methylcellulose (0.25% MC) or olive oil were administered orally by gavage nineteen hours following the yeast injection. Body temperatures were taken and recorded one hour after compound administration. Aspirin (300 mg/kg) was the reference standard drug administered with each antipyretic study. The mean temperature of the compound-treated groups, positive control group (Aspirin) and negative control group (vehicle) were calculated at 18 hours and 20 hours. The data was analyzed statistically using a paired-samples Student's t-Test.

TABLE VII

| Compounds | Change in Temperature (°C.) 18-20 Hour Period[1] |
|---|---|
| 0.25% MC | +0.10 |
| Aspirin (300 mg/kg) | −2.05 |
| Example 1 (300 mg/kg) | −1.55 |

(1) All decreases in temperature were significant at $p < 0.05$ using a paired-samples student's t-Test.

EXAMPLE 30

Adjuvant Arthritis Assay; Established

Chronic anti-inflammatory and antiarthritic activity were evaluated using the method described by S. Wong in "Tolmetin; A New Non-Steroidal Anti-inflammatory Agent" Editor: John R. Ward, Excerpta Medica, N.J., pp. 1-27 (1976). On day 19 post adjuvant all rats were evenly distributed according to edema size. Doses of treatment or vehicle were administered orally to all rats once daily on days 19-22 inclusive. Final paw volumes were determined on day 23 post adjuvant.

TABLE VIII

| Compound | $ED_{50}$ (mg/kg) |
|---|---|
| Example 1 | 36 |
| NAPROXEN | 28 |

What is claimed is:

1. A compound of the formula:

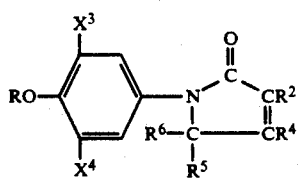

wherein:
R is a member selected from the group consisting of hydrogen, alkyl, alkanoyl and aroyl;
$R^2$ and $R^4$ are joined to form an unsaturated hydrocarbylene chain having four carbon atoms between their points of attachment to the heterocyclic ring;
$R^5$ and $R^6$ are the same or different and represent a member selected from the group consisting of hydrogen and lower alkyl; and
$X^3$ and $X^4$ are the same or different and represent a member selected from the group consisting of tertiary-alkyl and trimethylsilyl; and the non-toxic pharmacologically acceptable salts thereof.

2. The compound according to claim 1 wherein $X^3$ and $X^4$ represent tert-butyl.

3. The compound according to claim 1 wherein the unsaturated hydrocarbylene chain is 1,3-butadienylene.

4. A compound according to claim 1 of the formula:

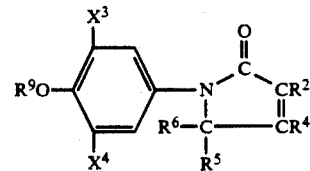

wherein:
$R^2$ and $R^4$ are joined to form an unsaturated hydrocarbylene chain having four carbon atoms between their points of attachment to the heterocyclic ring;
$R^5$ and $R^6$ are the same or different and represent a member selected from the group consisting of hydrogen and lower alkyl;
$R^9$ is selected from the group consisting of hydrogen, lower alkyl, alkanoyl and aroyl; and
$X^3$ and $X^4$ are the same or different tertiary-lower alkyl moieties; and the non-toxic pharmacologically acceptable salts thereof.

5. The compound according to claim 4 wherein $X^3$ and $X^4$ represent tert-butyl.

6. The compound according to claim 4 wherein $R^5$ and $R^6$ represent hydrogen.

7. The compound according to claim 5 wherein $R^9$ is hydrogen.

8. N-(3,5-Di-tert-butyl-4-hydroxyphenyl)isoindolinone.

9. A pharmaceutical composition comprising as the active ingredient a compound of the formula:

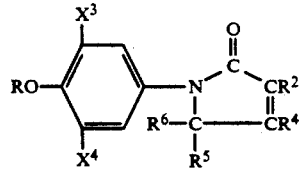

wherein:
R is a member selected from the group consisting of hydrogen, alkyl, alkanoyl and aroyl;
$R^2$ and $R^4$ are joined to form an unsaturated hydrocarbylene chain having four carbon atoms between their points of attachment to the heterocyclic ring;
$R^5$ and $R^6$ are the same or different and represent a member selected from the group consisting of hydrogen and lower alkyl; and
$X^3$ and $X^4$ are the same or different and represent a member selected from the group consisting of tertiary-alkyl and trimethylsilyl; or a non-toxic pharmacologically acceptable salt thereof; in combination with a pharmaceutically acceptable carrier.

10. The pharmaceutical composition according to claim 9 wherein the active ingredient is a compound in which $X^3$ and $X^4$ are tert-butyl.

11. A pharmaceutical composition according to claim 9 in which the active ingredient is a compound of the formula:

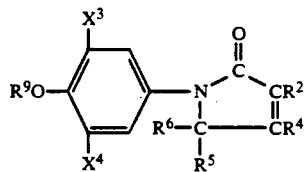

wherein:

$R^2$ and $R^4$ are joined to form an unsaturated hydrocarbylene chain having four carbon atoms between their points of attachment to the heterocyclic ring;

$R^5$ and $R^6$ are the same or different and represent a member selected from the group consisting of hydrogen and lower alkyl;

$R^9$ is selected from the group consisting of hydrogen, lower alkyl, alkanoyl and aroyl; and $X^3$ and $X^4$ are the same or different tertiary-lower alkyl moieties; or a non-toxic pharmacologically acceptable salt thereof; in combination with a pharmaceutically acceptable carrier.

12. The pharmaceutical composition according to claim 11 wherein the active ingredient is a compound in which $X^3$ and $X^4$ are tert-butyl.

13. The pharmaceutical composition according to claim 12 wherein the active ingredient is a compound in which $R^2$ and $R^4$ are joined to form a 1,3-butadienylene chain.

14. The pharmaceutical composition according to claim 11 wherein the active ingredient is N-(3,5-di-tert-butyl-4-hydroxyphenyl)isoindolinone.

15. A method for treating inflammation in a mammal which comprises administering a safe and effective amount of an active ingredient of the formula:

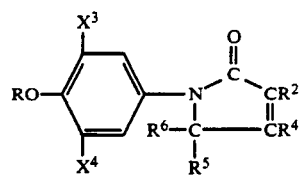

wherein:

R is a member selected from the group consisting of hydrogen, alkyl, alkanoyl and aroyl;

$R^2$ and $R^4$ are joined to form an unsaturated hydrocarbylene chain having four carbon atoms between their points of attachment to the heterocyclic ring;

$R^5$-$R^6$ are the same or different and represent a member selected from the group consisting of hydrogen and lower alkyl; and $X^3$ and $X^4$ are the same or different and represent a member selected from the group consisting of tertiary-alkyl and trimethylsilyl; or a non-toxic pharmacologically acceptable salt thereof.

16. The method according to claim 15 wherein the active ingredient is administered orally.

17. The method according to claim 15 wherein $R^2$ and $R^4$ are joined to form a 1,3-butadienylene chain.

18. The method according to claim 15 wherein $X^3$ and $X^4$ represent tert-butyl.

19. The method according to claim 15 wherein the active ingredient is a compound of the formula:

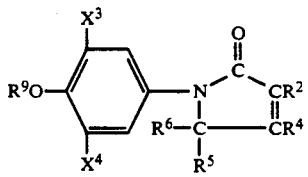

wherein:

$R^2$ and $R^4$ are joined to form an unsaturated hydrocarbylene chain having four carbon atoms between their points of attachment to the heterocyclic ring;

$R^5$ and $R^6$ are the same or different and represent a member selected from the group consisting of hydrogen and lower alkyl;

$R^9$ is selected from the group consisting of hydrogen, lower alkyl, alkanoyl and aroyl; and $X^3$ and $X^4$ are the same or different tertiary-lower alkyl moieties; or a non-toxic pharmacologically acceptable salt thereof.

20. The method according to claim 19 wherein the active ingredient is N-(3,5-di-tert-butyl-4-hydroxyphenyl)isoindolinone.

* * * * *